United States Patent [19]
Abbott et al.

[11] Patent Number: 5,338,286
[45] Date of Patent: Aug. 16, 1994

[54] ELECTROMAGNETIC BIORESPONSE BY SELECTIVE SPECTRAL SUPPRESSION IN PULSED FIELD STIMULATION

[75] Inventors: Joan Abbott, New York, N.Y.; Richard Cangialosi, Branchville; Brian A. Pethica, Upper Montclair, both of N.J.

[73] Assignee: Electro-Biology, Inc., Parsippany, N.J.

[21] Appl. No.: 987,461

[22] Filed: Dec. 8, 1992

[51] Int. Cl.$^5$ .............................................. A61N 1/00
[52] U.S. Cl. ...................................... 600/14; 607/50
[58] Field of Search ............................... 600/9, 13-14; 128/419 F, 421, 422; 607/48-52, 61, 65, 72, 76

[56] References Cited

U.S. PATENT DOCUMENTS

| | | |
|---|---|---|
| 3,893,462 | 7/1974 | Manning . |
| 4,105,017 | 8/1978 | Ryaby et al. . |
| 4,266,532 | 5/1981 | Ryaby et al. . |
| 4,266,533 | 5/1981 | Ryaby et al. . |
| 4,315,503 | 2/1982 | Ryaby et al. . |
| 4,467,808 | 8/1984 | Brighton et al. . |
| 4,574,809 | 3/1986 | Talish et al. . |
| 4,641,633 | 2/1987 | Delgado . |
| 4,683,873 | 8/1987 | Cadossi et al. . |
| 4,793,325 | 12/1988 | Cadossi et al. . |
| 4,818,697 | 4/1989 | Liboff et al. . |
| 4,993,413 | 2/1991 | McLeod et al. . |
| 4,998,532 | 3/1991 | Griffith . |
| 5,014,669 | 5/1991 | Pollack et al. . |

FOREIGN PATENT DOCUMENTS 1113156 11/1981 Canada ............................... 600/14

OTHER PUBLICATIONS

Goodman et al., "Exposure of Human Cells to Low-frequency Electromagnetic Field Results in Quantitative Changes in Transcripts," *Biochimica et Biophysica Acta* 1009:216-220 (1989).

Rubin et al., "Prevention of Ostoporosis by Pulsed Electromagnetic Fields," *The Journal of Bone and Joint Surgery* 71-A(3):411-417 (Mar. 1989).

Goodman et al., "Stimulation of RNA Synthesis in the Salivary Gland Cells of Sciara Coprophila by an Electromagnetic Signal Used for Treatment of Skeletal Problems in Horses," *Journal of Bioelectricity* 6(1):37-47 (1987).

Schematic for Electro-Biology, Inc. Equine Unit circa 1985.

Primary Examiner—Kyle L. Howell
Assistant Examiner—John Lacyk
Attorney, Agent, or Firm—Woodard, Emhardt, Naughton, Moriarty & McNett

[57] ABSTRACT

A noninvasive apparatus for treating living tissue and cells by means of a pulsed electromagnetic field, and particularly suitable for bone growth stimulation. A treatment coil is noninvasively mounted in proximity to an afflicted body part to be treated, and an electronic generator coupled to said treatment coil generates pulses having a positive pulse portion 200 to 250 microseconds in duration and a negative pulse portion having a duration less than approximately 50 microseconds, the pulses further characterized by a smooth transition at least from the leading edge to a relatively flat top segment. High-frequency content is substantially reduced, particularly at frequencies above 200 kHz.

18 Claims, 5 Drawing Sheets

ELECTROMAGNETIC BIORESPONSE BY SELECTIVE SPECTRAL SUPPRESSION IN PULSED FIELD STIMULATION

BACKGROUND OF THE INVENTION

This invention relates to the treatment of living tissue or cells with electromagnetic fields, and particularly to such treatment employing pulsed electromagnetic fields (PEMFs).

It is well known that time-varying low-energy electric or magnetic fields produce a range of responses in biological systems. In particular, low-energy fields which are essentially athermal are increasingly used for therapeutic purposes as in the healing of fractures and ulcers, assisting bone graft incorporation, etc. The precise mechanisms of action of these low-energy fields are not well understood, but there is evidence that the responses relate to the direct effects of both magnetic and electric fields. Magnetic fields may also act through the induction of electric fields in tissue or cells, and time-varying electric fields may be imposed by induction, capacitative coupling or by use of implanted electrodes.

A variety of time-varying electromagnetic inputs (waveforms) have been studied, patented and used in practice. The widest present application is of electric field inputs to tissue induced by an asymmetrically rising and falling magnetic field as described, e.g., in the following patents:

| Patent No. | Inventor | Issue Date |
| --- | --- | --- |
| 3,893,462 | Manning | Jul. 8, 1975 |
| 4,105,017 | Ryaby et al. | Aug. 8, 1978 |
| 4,266,532 | Ryaby et al. | May 12, 1981 |
| 4,266,533 | Ryaby et al. | May 12, 1981 |
| 4,315,503 | Ryaby et al. | Feb. 16, 1982 |
| 4,683,873 | Cadossi et al. | Aug. 4, 1987 |

The waveforms of these induced electric inputs are generally described by a quasi-rectangular or trapezoidal-shaped excursion of the electric (E) field followed either by a narrower excursion of higher amplitude in the reverse direction in the case of pulse trains or "bursts," or by a broad low-amplitude excursion in the case of some repetitive single pulses. It is also known from, e.g., U.S. Pat. Nos. 4,998,532 to Griffith and 5,014,699 to Pollack, that more symmetrical pulsed fields produced, for example, by switching abruptly between positive and negative electric fields (achieved, for example, by switching the polarity of the current input to a low inductance coil to give a series of rising and falling magnetic fields in the target tissue or cell system) are also bioactive.

A characteristic of the waveforms in these cases is that abrupt changes occur in the magnitudes or directions of the electric or magnetic fields. For example, in commercial application of the waveforms described by Ryaby et al., the induced electric field rises from zero to its quasi-rectangular "positive" ongoing form or reverses sign to a higher-amplitude narrow "negative" excursion in a time interval of about one microsecond or less, as compared to pulse widths typically on the order of tens to thousands of microseconds. Correspondingly, the time derivative of the magnetic field changes sign over an interval of about one microsecond, whereas the intervals in which the sign is unchanged are typically ten or more times as long. In the work of Griffith and Pollack, the preferred pulse widths are on the order of ten microseconds, these pulses being repeated in bursts on the order of milliseconds. The reversal time for these pulses is typically one microsecond or less. Trains of pulses as in the above-referenced Ryaby et al. patents, all of which are hereby incorporated by reference, typically last for milliseconds and the pulses or pulse trains are repeated at intervals on the order of tens to thousands of milliseconds. Still, in commercially available equipment generating such pulse trains, the rise and fall times for individual pulses are abrupt, i.e., about one microsecond or less.

In some cases, the abrupt changes in the time derivative of the electric field may be associated with overshooting, which may include a damped oscillation or ringing on the order of 1 MHz, i.e., within the range of about 0.5 to 5 MHz. The frequency content of asymmetric pulse waveforms of the Ryaby et al. type, as derived by discrete Fourier Transforms, can range to 10 MHz, as described by Goodman et al. in a paper entitled "Exposure of Human Cells to Low-Frequency Electromagnetic Fields Results in Quantitative Changes in Transcripts," in Biochimica et Biophysica Acta, 1009 (1989) 216–220.

SUMMARY OF THE INVENTION

We have discovered that the known biological and therapeutic stimulation by pulsing magnetic fields or by pulsing induced or direct electric fields as practiced with the application of pulses which have heretofore been configured with rapid changes in magnitude or direction of the fields can be improved significantly by modifying the configuration of these pulses to selectively reduce the higher-frequency components of the equivalent spectrum. In terms of the time domain, significant improvement in the bioefficacy of low-energy pulsed electromagnetic signals configured with waveforms ordinarily characterized by abrupt changes in magnitude or sign of the electric or magnetic field is achievable by reducing or eliminating one or more of the previously characteristic abrupt changes and providing smoother transitions to relatively flat segments or portions of the signal or waveform. "Abrupt" in this context is intended to connote time intervals of approximately 1 microsecond or less.

According to one aspect of the present invention, a noninvasive apparatus for treating living tissue and cells by means of a pulsed electromagnetic field characterized by field direction changes typically fast enough to result in substantial high-frequency content is provided with circuitry for improving bioresponse by selectively reducing the high-frequency content of the pulses.

According to another aspect of the invention, a noninvasive apparatus for treating living tissue and cells by means of a pulsed electromagnetic field, in which a treatment coil is noninvasively mounted in proximity to an afflicted body part to be treated, is provided with electronic generator circuitry coupled to the treatment coil for generating pulses having a leading edge, a trailing edge and a relatively flat segment therebetween, the pulses characterized by a smooth transition on at least one of the edges immediately adjacent the relatively flat segment.

It is a general object of the present invention to provide improved bioresponse by selective spectral suppression in a PEMF signal.

A further object is to make presently known and used signals more effective by modifying them to create one or more smoother transitions between desired signal levels.

These and other objects and advantages of the present invention will be more apparent upon reading the following detailed description of the preferred embodiment in conjunction with the accompanying drawings.

DESCRIPTION OF THE PREFERRED EMBODIMENT

Figure 1:
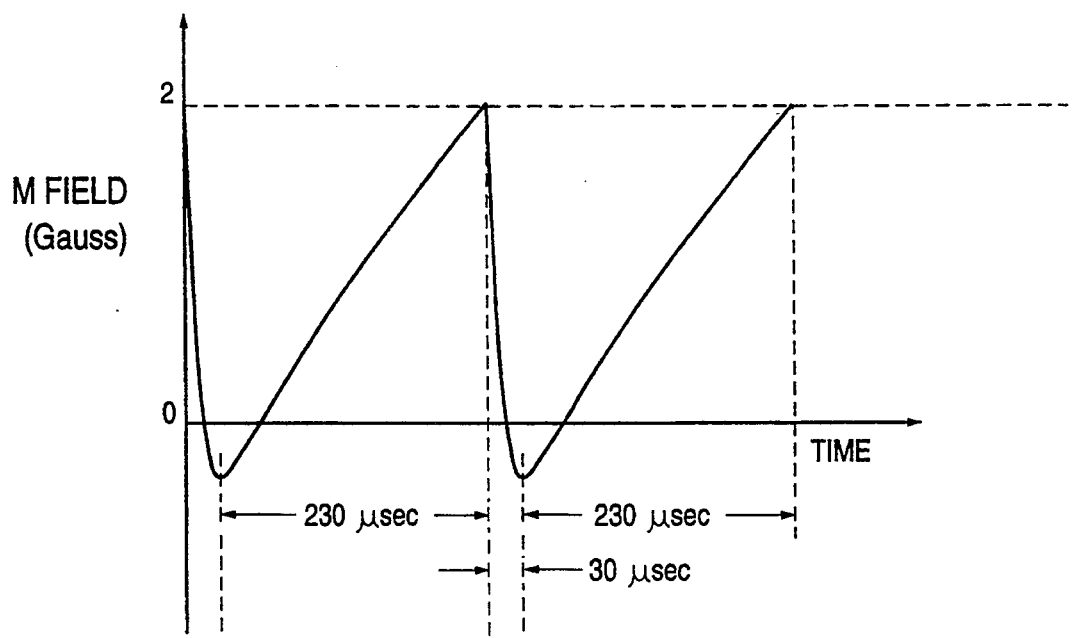
FIG. 1 illustrates tile magnetic field waveform according to the preferred embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates, for example, in the use of signal forms as herein described delivered by capacitative or implanted electrodes.

Figure 2:
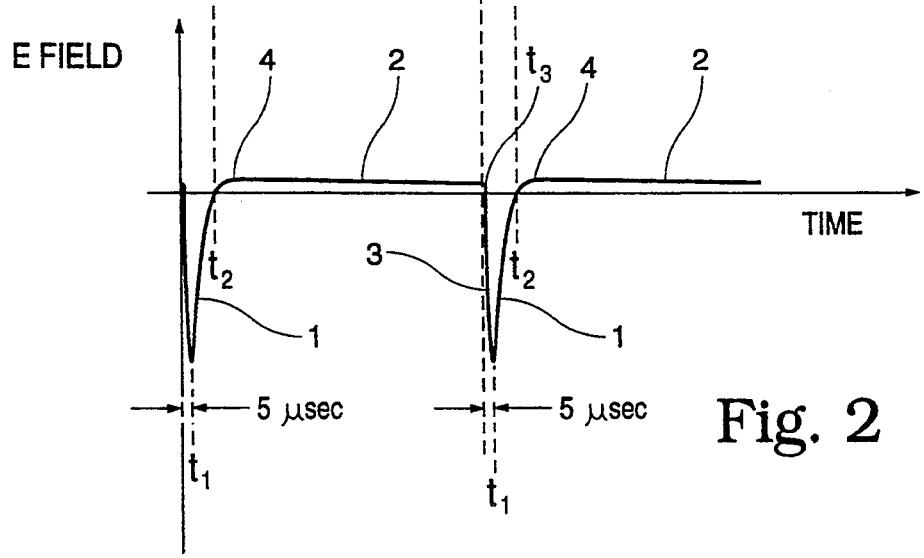
FIG. 2 illustrates the induced electric field waveform according to the preferred embodiment of the present invention.

FIGS. 1 and 2 illustrate the magnetic (M) field waveform and corresponding induced electric (E) field waveform, respectively, for a stimulatory waveform for use in bone and tissue healing according to the preferred embodiment of the present invention. The waveform of FIG. 2 represents the electric field, as would be measured with a suitable inductive pickup, which is produced by induction from the magnetic field of FIG. 1 passing through the tissue or cells. Those skilled in the art will appreciate that the relationship between the waveforms of FIGS. 1 and 2 are readily related in that the induced electric field is directly proportional to the time derivative of the magnetic field. FIG. 2 also corresponds to the waveform of the voltage across the treatment coil driven by the preferred embodiment of a signal generator according to the present invention, which will be described with reference to FIG. 7. The principles of tile invention will apply equally to single repetitive pulses or to pulse trains as described in the above-referenced Ryaby et al. patents, and it is to be understood that FIGS. 1 and 2 represent a portion of a pulse burst sufficient to show the details of an individual pulse as well as the transition between pulses in the pulse burst.

It has been found that the bioresponse of PEMF signals is sharply improved when the rise and fall times in the electric field are lengthened, and, in particular, when the amplitude changes are made less abrupt by rounding the profile of the pulses. An example of such rounding is shown in FIG. 2, particularly in the approximately exponential shape of leading edge 1 of an individual pulse having a relatively flat top segment 2 and a trailing edge 3, the pulse having a smooth transition 4 from leading edge 1 to the relatively flat top segment 2 as shown in the drawing. The rounding will usually be associated with some increase in the rise and fall times, as is also shown in FIG. 2, in which the time interval from time $t_1$ to time $t_2$, when the E field signal crosses zero, is 25 microseconds, and the time to reach the signal maximum from $t_1$ is about 30 microseconds, with the signal generator and treatment coil to be described with reference to FIG. 7. The corresponding fall time, i.e., the interval from $t_3$ to $t_1$, is 5 microseconds. Most preferably, the leading edge is continuously smooth for the entire interval from $t_1$ to the signal maximum, and the trailing edge is continuously smooth for the entire interval from $t_3$ to $t_1$. That is, there is no discontinuity in the signal or abrupt portion associated with either edge.

The circuitry to be described produces the desired rounding while maintaining the amplitude of the signal over most of its relatively flat top segment 2, whereas the negative amplitudes of pulse trains of the Ryaby et al. type after smoothing will usually not be as high. In the case of certain single repetitive pulses as described in the Ryaby et al. patents, in which relatively shallow, long negative excursions are effective, the positive and negative amplitudes of the electric field are readily maintained over most of the relevant excursion periods, and the changes in the overall waveform constitute primarily an extension of the rise and fall times and a rounding of the terminal portion of the rising and trailing edges. It is to be understood that "positive" and "negative" as well as terms such as "rise" and "fall" time are intended as relative terms for reference purposes in the description of pulse portions of opposite polarity with respect to a reference potential level. It is contemplated that similar rounding and extension of the edges of sharp square-wave pulses such as taught by Griffith and Pollack et al. will similarly result in improved bioresponse. Rectangular pulses, quasi-rectangular pulses, and trapezoidal pulses, among others, are all considered to have a relatively flat top segment in the context of this invention, and improved bioresponse would be anticipated upon appropriate rounding of the profiles of such pulses in accordance with the teachings of this invention.

Figure 3:
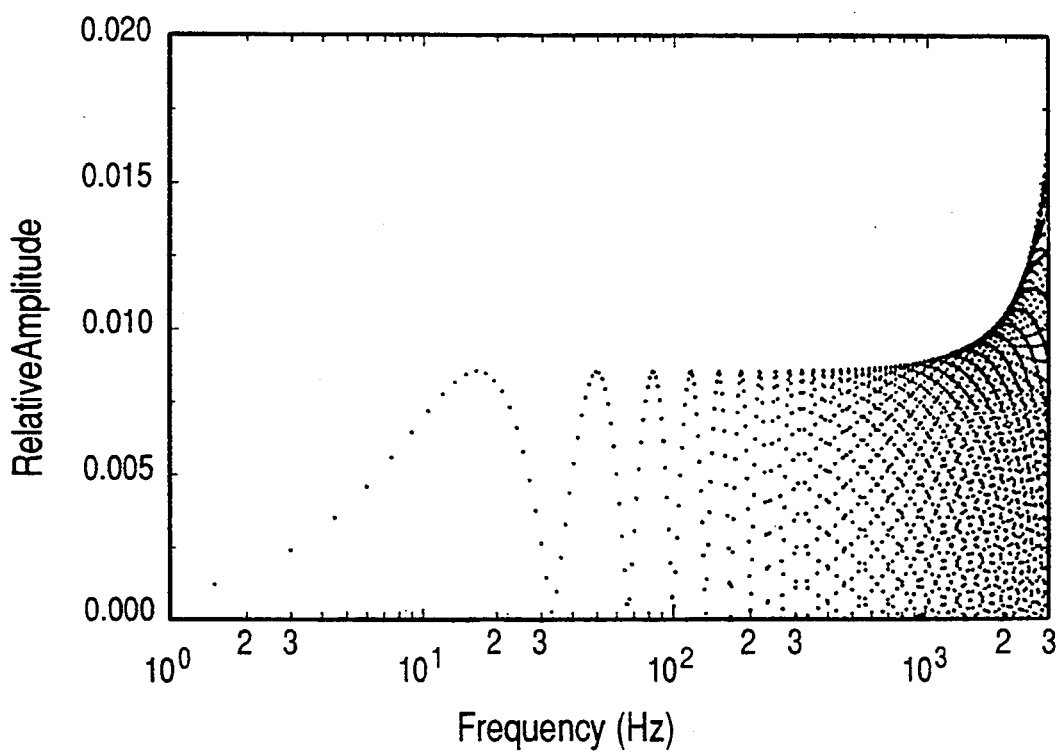
FIG. 3 illustrates the Fast Fourier Transform (FFT) of a basic form of an induced electric field signal (without smoothing) in a low frequency range.
Figure 4:
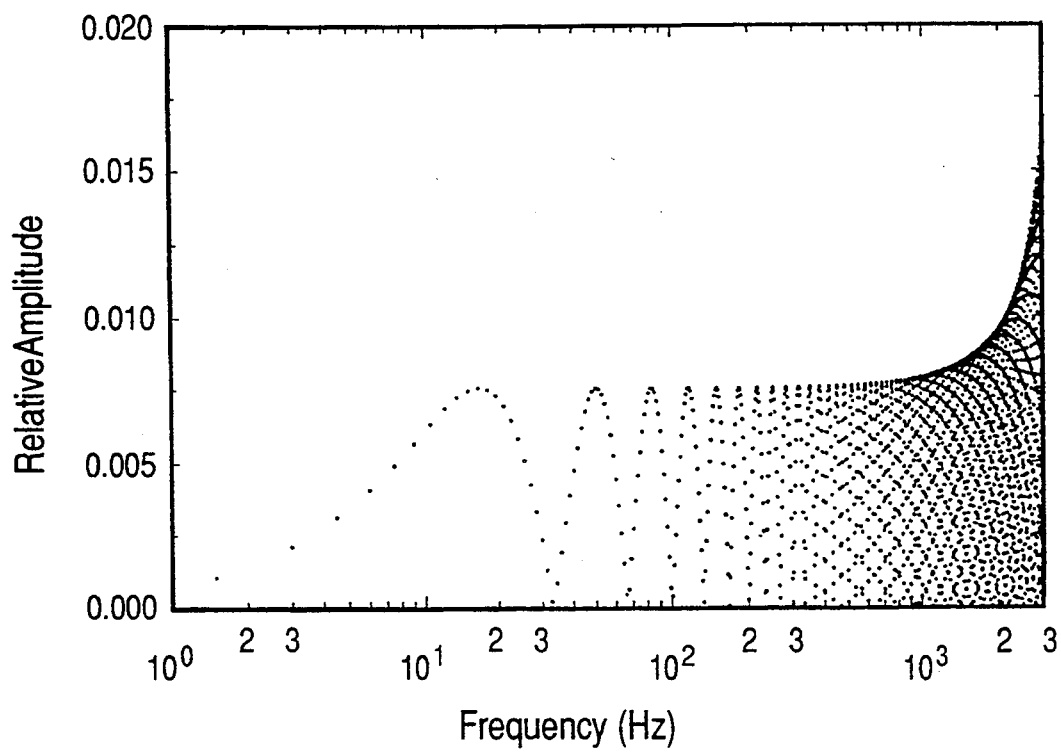
FIG. 4 illustrates the FFT of the induced electric field signal of FIG. 2 in a low frequency range.
Figure 5:
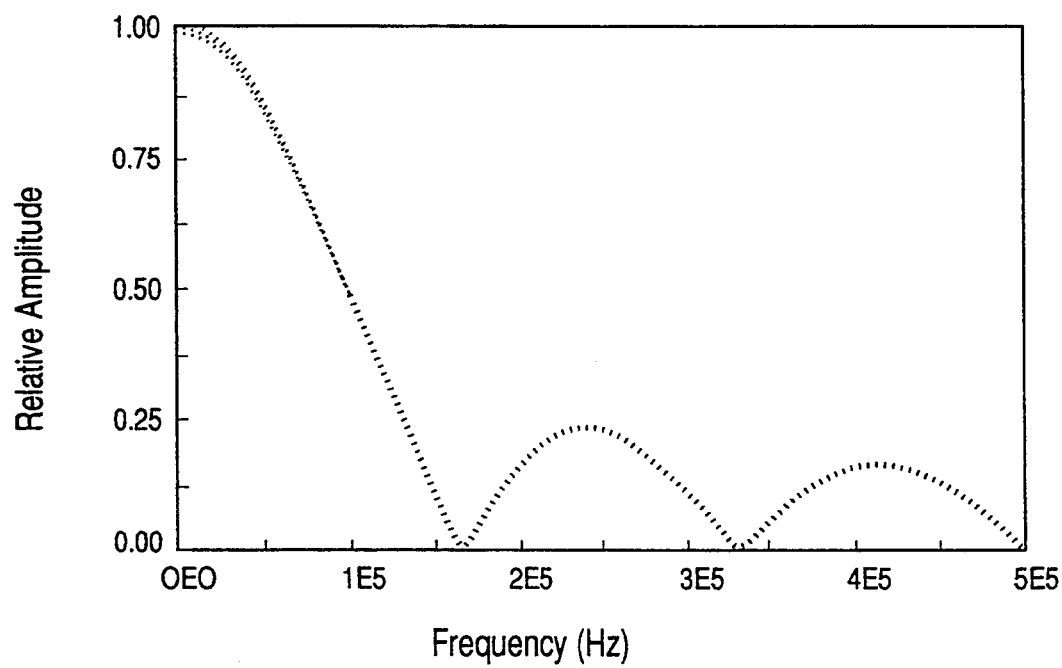
FIG. 5 illustrates the FFT of a basic form of an induced electric field signal (without smoothing) in a high frequency range.
Figure 6:
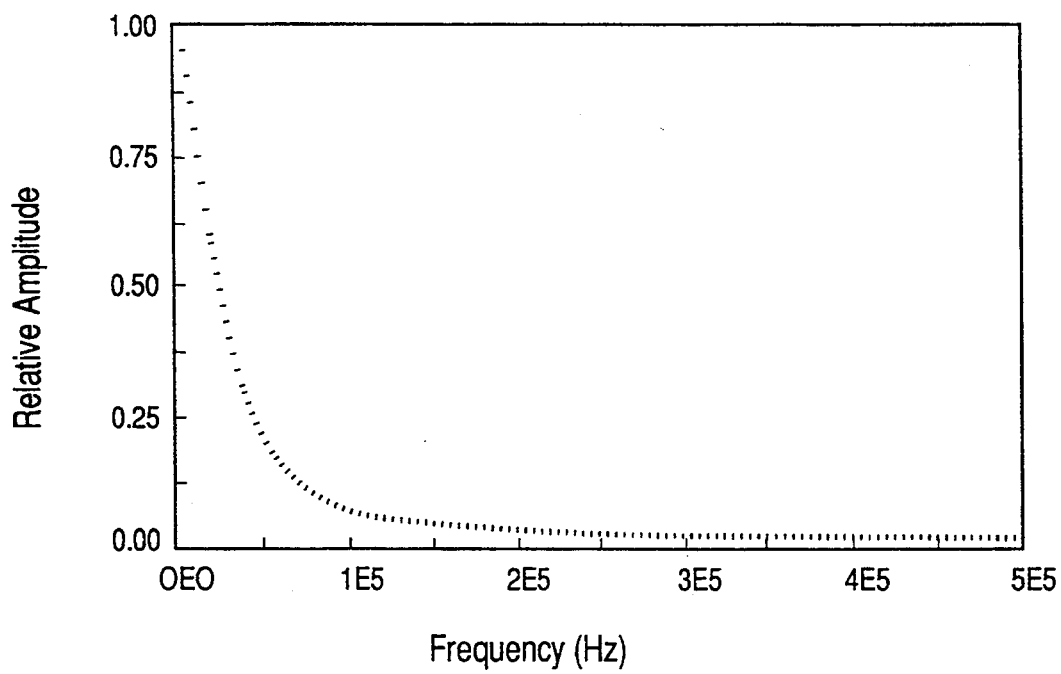
FIG. 6 illustrates the FFT of the induced electric field signal of FIG. 2 in a high frequency range.

The equivalent frequency-domain representation of the time-varying signal of FIG. 2 is shown in FIGS. 4 and 6, and, for comparison purposes, a basic form (without rounding) of an induced electric field signal in the frequency domain is illustrated in FIGS. 3 and 5, the basic form being characterized by abrupt changes in amplitude over about one microsecond at the leading and trailing edges of the pulses. The Fast Fourier Transforms of FIGS. 3-6 were all obtained from a pulse train signal having a pulse period of approximately 260 microseconds, approximately 230 microseconds of which is the positive pulse portion, a burst width of approximately 30 milliseconds, and a burst repetition rate of 1.5 Hz. FIGS. 3 and 4 illustrate clearly that the frequency spectra are equivalent for frequencies below 3 kHz, while FIGS. 5 and 6 illustrate clearly the great difference that exists between the spectra in the high frequency range extending up to 500 kHz (denoted as 5E5 in the drawings). As can be appreciated from FIGS. 5 and 6, frequency components above 50 kHz and particularly above 200 kHz are selectively reduced by the circuitry according to the preferred embodiment of the present invention. The frequency spectra of other signals presently used also include a large number of equivalent spectral lines including higher frequency components in the range of 50 kHz 5 MHz corresponding to tile abrupt edges, ramps, overshoot and ringing in those signals, and it is believed that the effectiveness of all such signals can be improved by selective reduction of component frequencies as described above.

Figure 7:
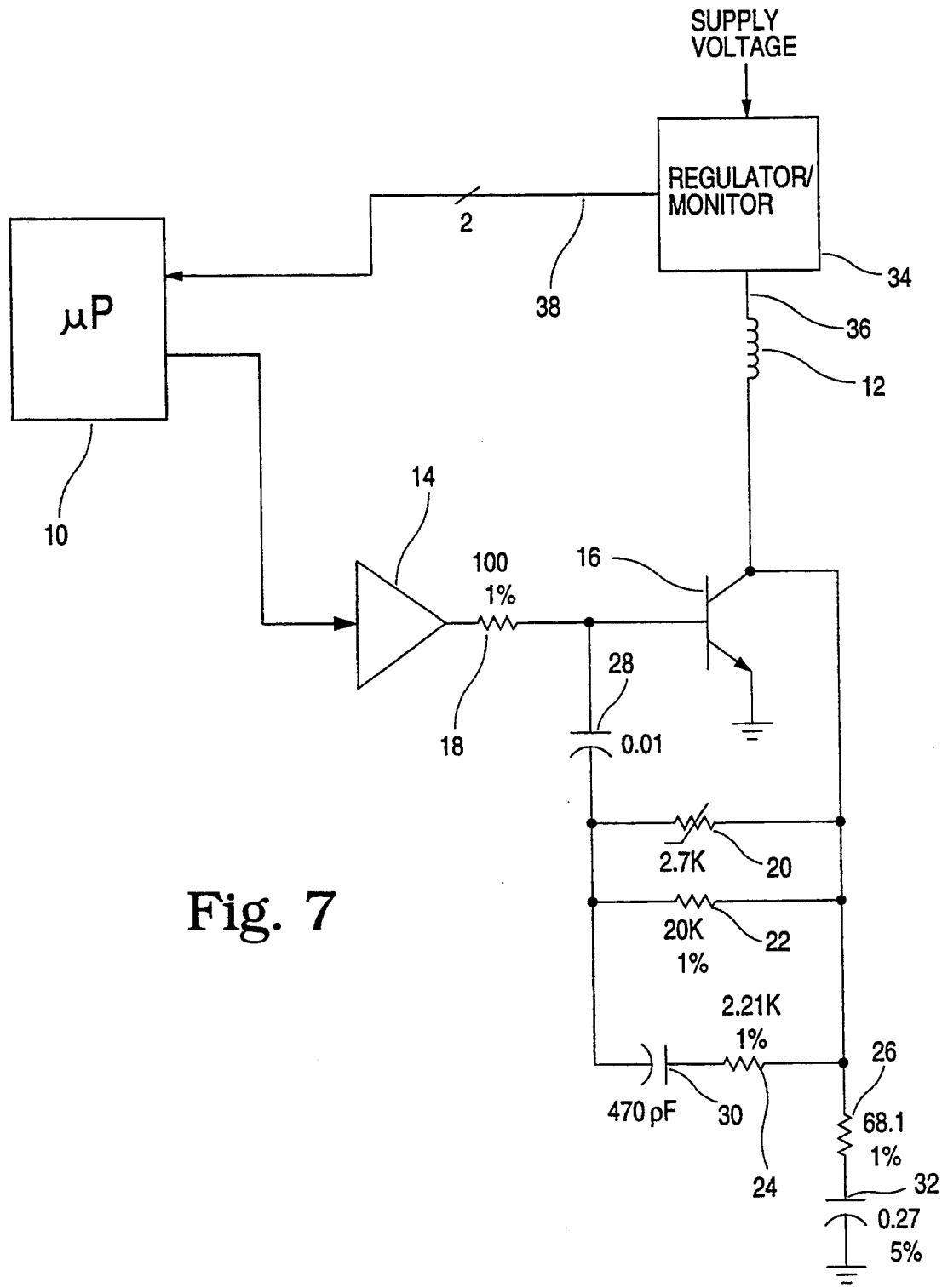
FIG. 7 is an electrical schematic of a pulse generator according to the preferred embodiment of the present invention.

Referring now to FIG. 7, a pulse generator capable of producing such improved bioresponse and, in particular, capable of producing the signals shown in FIGS. 1 and 2, will be described. The timing and pulse width of the individual pulses in each pulse train as well as the burst width and burst repetition rate are controlled by a microprocessor 10 which is appropriately programmed for such purposes in a manner well known to those skilled in the art. Further description of control units for control of such parameters, as well as circuitry designed to accommodate changes in pulse width and repetition rate, for example, in the course of a given body treatment according to a predetermined pattern or program of variation, may be found in the above-referenced U.S. Pat. No. 4,315,503 to Ryaby et al., and such descriptions in particular are hereby incorporated by reference along with the entirety of said patent. Microprocessor 10 generates a drive signal for the treatment coil 12, the drive signal as supplied by the microprocessor taking the form of bursts of individual square-wave pulses. In the drive signal corresponding to the signals of FIGS. 1 and 2, each has a pulse width of approximately 230 microseconds, followed by a 30-microsecond interval prior to the next pulse, and the pulses are supplied in 30-millisecond bursts at a repetition rate of 1.5 Hz.

The microprocessor supplies the drive signal through driver amplifier 14 to a signal shaping circuit built around a transistor 16 and including resistors 18, 20, 22, 24 and 26 and capacitors 28, 30 and 32 interconnected as shown in the drawing. Resistors 18, 20 and 22 and capacitor 28 form a negative voltage shunt feedback loop to control the signal negative amplitude. Resistor 20 is a positive temperature coefficient (PTC) device which compensates for $V_{BE}$ temperature variations in transistor 16. Capacitor 30 and resistor 24 control the trailing edge slope of the signal, while capacitor 32 and resistor 26 control the leading edge slope. The waveform of FIG. 2 corresponds to the component values shown in FIG. 7, with a treatment coil with an inductance of about 500 millihenries. One such treatment coil is the FLX-2 coil, and, for different applications, one may employ other coils in the FLX family line, all commercially available from Electro-Biology, Inc. Other values of treatment coil inductance are disclosed in the above-referenced Ryaby et al. patents incorporated herein by reference.

A regulated voltage level of approximately 1 volt DC is established by a regulator/monitor circuit 34, one output of which is connected to treatment coil 12 via line 36. Regulator/monitor 34 also has a pair of output lines 38 to the microprocessor for monitoring purposes to be described.

Figure 8:
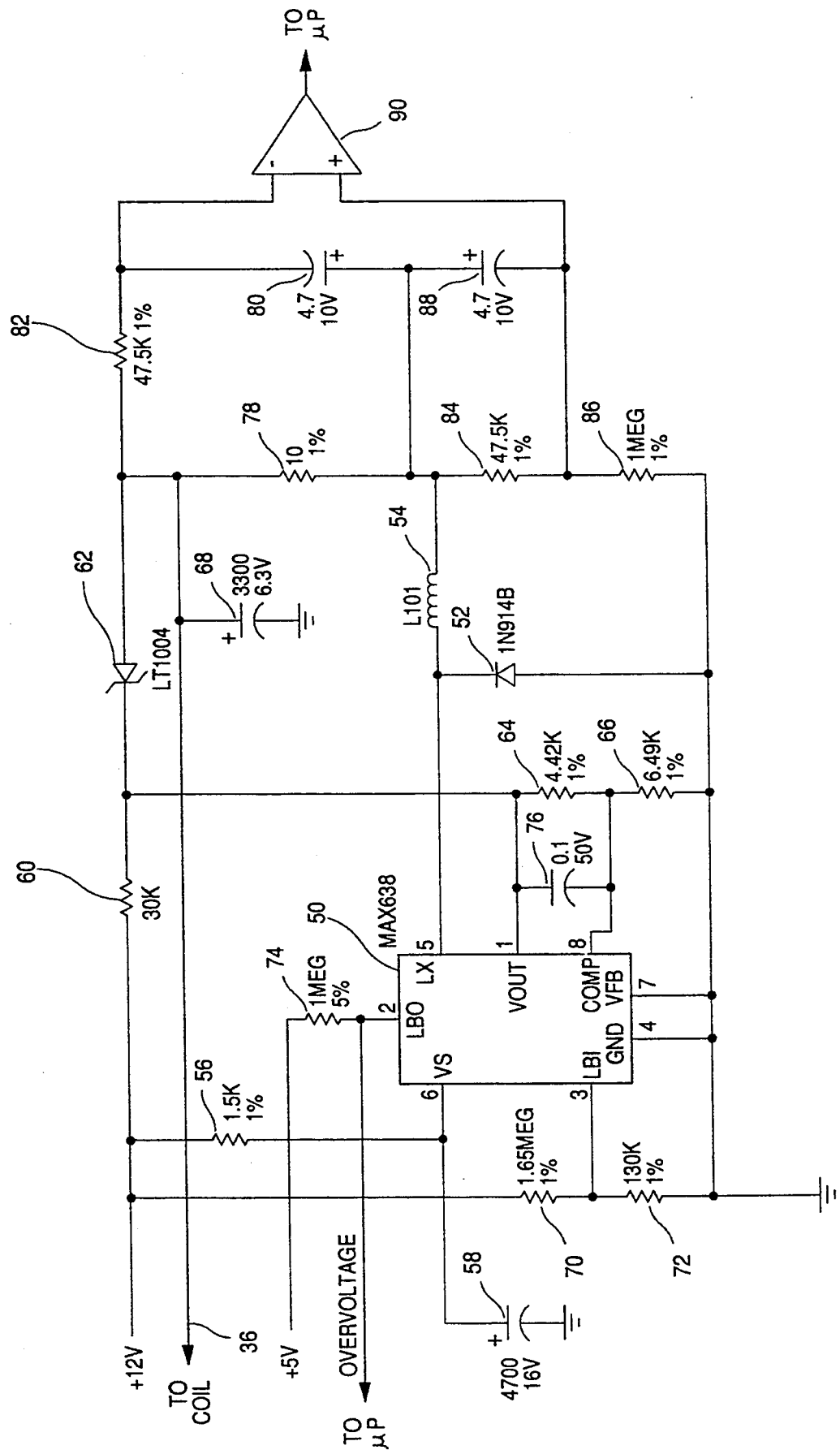
FIG. 8 is an electrical schematic of the regulator/monitor shown in FIG. 7.

Regulator/monitor 34, as shown in further detail in FIG. 8, includes an integrated circuit (IC) 50 which, in conjunction with diode 52 and inductor 54, forms a stepdown switching regulator. Battery power (+12 volts DC) is applied through current-limiting resistor 56 and filter capacitor 58 to pin 6 of IC 50, which is preferably a MAX638 IC commercially available from Maxim Integrated Products. The output voltage is raised from 1.0 volt to 2.25 volts by resistor 60 and diode 62 in order to match the internal comparator 1.31 volt reference of IC 50. Resistor 64 and resistor 66 form an external voltage divider to set the output voltage to 1.0 VDC on output filter capacitor 68 and output line 36 to the coil. Resistors 70 and 72 form a voltage reference on the device low battery input (LBI) pin 3. If the battery voltage exceeds the threshold set by this resistor divider, an overvoltage condition is set by the device low battery output (LBO) pin 2 and resistor 74. This overvoltage signal is returned to the microprocessor on one of the lines 38 previously mentioned.

Regulator/monitor circuit 34 also includes an alarm circuit the purpose of which is to monitor and control the field strength of the signal in the treatment coil. Basic signal parameters are established by IC 50 providing a constant voltage level of 1 VDC, as previously described, to drive the treatment coil for a duration controlled by transistor 16 in the pulse-shaping circuit shown in FIG. 7.

Variations of the treatment coil inductance are monitored by current-sensing resistor 78. As the current in the treatment coil increases due to an inductance decrease, the charge on capacitor 80 will increase during tile pulse burst. After the pulse burst, the time required for capacitor 80 to discharge through resistor 82 to the reference voltage established by resistors 84 and 86 and capacitor 88 is detected by the microprocessor through a comparator 90. The microprocessor counts its internal fixed-rate pulses during this time period and displays an error message if the number of counts exceeds the internal limits set for each coil type.

In addition to the methods already described for increasing the required time constant to round or smooth the abrupt edges, the inductance of the treatment coil may be increased or, in the case of a capacitively coupled electric signal, series resistance can be added to increase tile time constant to, e.g., 5 milliseconds. Alternatively, resonant circuits using series/parallel arrangements of resistors, inductors and capacitors, including the values for the primary delivery element for the desired localized field, i.e., the coil or capacitor placed at the treatment site or used to stimulate tissue cultures, etc., may be employed.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A noninvasive apparatus for treating living tissue and cells by means of a pulsed electromagnetic field, comprising:
    means for generating a drive signal including a series of pulses having high-frequency components associated with abrupt changes in value; and means responsive to said drive signal for generating a pulsed field effective to produce a therapeutic bioresponse when coupled to an afflicted body part to be treated, said pulsed field generating means including signal shaping means for selectively reducing signal components of said drive signal at frequencies above 50 kHz.

2. The apparatus of claim 1 wherein said signal shaping means includes means for producing a substantially flat frequency spectrum for frequencies above 200 kHz.

3. The apparatus of claim 2, wherein said pulses each include a pulse portion with a duration greater than approximately 200 microseconds and an opposite-polarity pulse portion with duration less than approximately 50 microseconds.

4. The apparatus of claim 3, wherein said generating means includes means for generating said pulses in pulse bursts each containing at least approximately 100 pulses, and means for generating said pulse bursts at a repetition rate of approximately 1.5 Hz.

5. The apparatus of claim 2, wherein said pulses each generating means includes means for generating repetitive single pulses at a pulse repetition rate of approximately 10 to 100 Hz. portion with duration less than approximately 50 microseconds.

6. The apparatus of claim 1, wherein pulses each include a pulse portion with a duration greater than approximately 200 microseconds and an approximately 50 microseconds.

7. The apparatus of claim 1, wherein said generating means includes means for generating said pulses in pulse bursts each containing at least approximately 100 pulses, and means for generating said pulse bursts at a repetition rate of approximately 1.5 Hz.

8. The apparatus of claim 1, wherein said generating means includes means for generating repetitive single pulses at a pulse repetition rate of approximately 10 to 100 Hz.

9. A noninvasive apparatus for treating living tissue and cells by means of a pulsed electromagnetic field, comprising:

a treatment coil;
means for noninvasively mounting said treatment coil in proximity to an afflicted body part to be treated; and
electronic generator means coupled to said treatment coil for generating pulses each having a leading edge, a trailing edge and a relatively flat peak therebetween, said pulses having a smooth transition on at least one of said edges immediately adjacent said relatively flat peak.

10. The apparatus of claim 9, wherein said pulses have a smooth transition on both of said edges immediately adjacent said relatively flat segment.

11. The apparatus of claim 10, wherein said leading edge has a duration of at least approximately 10 microseconds.

12. The apparatus of claim 10, wherein said trailing edge has a duration of at least approximately 10 microseconds.

13. The apparatus of claim 12, wherein said electronic generator means includes means for generating repetitive single pulses at a pulse repetition rate of approximately 10 to 100 Hz.

14. The apparatus us of claim 12, wherein said electronic generator means includes means for generating said pulses in pulse bursts at a repetition rate of approximately 1.5 Hz.

15. The apparatus of claim 9, wherein said leading edge has a duration of at least approximately 10 microseconds.

16. The apparatus of claim 9, wherein said trailing edge has a duration of at least approximately 10 microseconds.

17. The apparatus of claim 9, wherein said electronic generator means includes means for generating repetitive single pulses at a pulse repetition rate of approximately 10 to 100 Hz.

18. The apparatus of claim 9, wherein said electronic generator means includes means for generating said pulses in pulse bursts at a repetition rate of approximately 1.5 Hz.

* * * * *

UNITED STATES PATENT AND TRADEMARK OFFICE
CERTIFICATE OF CORRECTION

PATENT NO. : 5,338,286
DATED : August 16, 1994
INVENTOR(S) : Joan Abbott et al.

It is certified that error appears in the above-identified patent and that said Letters Patent is hereby corrected as shown below:

In column 3, line 19, please change "FIG," to --FIG.--.
In column 3, line 64, please change "tile" to --the--.
In column 5, line 13, please change "tile" to --the--.
In column 6, line 34, please change "tile" to --the--.
In column 6, line 47, please change "tile" to --the--.
In column 7, line 21, please delete "pulses each".
In column 7, lines 24-25, please delete "portion with duration less than approximately 50 microseconds."
In column 7, line 29, after "an" please insert: --opposite-polarity pulse portion with duration less than--.
In column 8, line 24, please delete "us".

Signed and Sealed this

Twenty-fifth Day of October, 1994

Attest:

BRUCE LEHMAN

Attesting Officer

Commissioner of Patents and Trademarks